(12) United States Patent
Kurata

(10) Patent No.: US 8,362,316 B2
(45) Date of Patent: Jan. 29, 2013

(54) WOUND DRESSING

(75) Inventor: Shuhei Kurata, Settsu (JP)

(73) Assignee: Zuiko Corporation, Osaka (JP)

( * ) Notice: Subject to any disclaimer, the term of this patent is extended or adjusted under 35 U.S.C. 154(b) by 403 days.

(21) Appl. No.: 12/308,563

(22) PCT Filed: May 25, 2007

(86) PCT No.: PCT/JP2007/060726
§ 371 (c)(1),
(2), (4) Date: Dec. 18, 2008

(87) PCT Pub. No.: WO2008/004380
PCT Pub. Date: Jan. 10, 2008

(65) Prior Publication Data
US 2010/0010462 A1    Jan. 14, 2010

(30) Foreign Application Priority Data

Jul. 6, 2006    (JP) .................................. 2006-186861
Jul. 28, 2006    (JP) .................................. 2006-205790

(51) Int. Cl.
*A61F 13/15*    (2006.01)
*A61F 13/00*    (2006.01)

(52) U.S. Cl. ............. 604/372; 604/367; 602/43; 602/41

(58) Field of Classification Search .................. 604/372, 604/367; 156/60; 424/445
See application file for complete search history.

(56) References Cited

U.S. PATENT DOCUMENTS 2,431,203 A * 11/1947 Sebastian ......................... 602/42
3,929,135 A * 12/1975 Thompson ............... 604/385.08
5,242,522 A * 9/1993 Moir ............................. 156/243
5,465,735 A    11/1995 Patel (Continued)

FOREIGN PATENT DOCUMENTS

| EP | 0 147 119 | 7/1985 |
| JP | 55-33785 | 3/1980 |
| JP | 7-136240 | 5/1995 |
| JP | 2004-520096 | 7/2004 |
| WO | WO-2005000372 A1 * | 1/2006 |

OTHER PUBLICATIONS

International Search Report issued Aug. 8, 2007 in the International (PCT) Application of which the present application is the U.S. National Stage.

(Continued)

*Primary Examiner* — Susan Su
(74) *Attorney, Agent, or Firm* — Wenderoth, Lind & Ponack, L.L.P.

(57) ABSTRACT

Provided is a further improved wound dressing suitable for a method for treating a wound while maintaining a moist environment created by exudate oozing from the wound. The wound dressing (5) comprises at least three layers including a first layer, a second layer and a third layer in order from the side used in contact with a wound site, which layers are integrally stacked together. The first layer (1) comprises a resin sheet material having a number of pores penetrating in a thickness direction. The second layer (2) comprises a sheet material of which the surface is water-repellent and becomes water-permeable when pressure is applied. The third layer (3) comprises a sheet material capable of absorbing and holding water. The wound dressing optionally comprises a fourth layer comprising a resin film, a fabric or a nonwoven.

9 Claims, 8 Drawing Sheets

U.S. PATENT DOCUMENTS

| | | | |
|---|---|---|---|
| 5,685,833 A * | 11/1997 | Turngren | 602/58 |
| 5,759,570 A | 6/1998 | Arnold | |
| 5,981,822 A | 11/1999 | Addison | |
| 6,566,577 B1 | 5/2003 | Addison et al. | |
| 7,459,598 B2 * | 12/2008 | Sigurjonsson et al. | 602/48 |
| 2003/0086963 A1 | 5/2003 | Scamilla Aledo et al. | |
| 2006/0094997 A1 * | 5/2006 | Kurata | 602/41 |

OTHER PUBLICATIONS

Japanese Office Action dated Dec. 14, 2010 in counterpart Japanese patent application No. JP 2008-523620.

Extended European Search Report issued Mar. 26, 2012 in corresponding European Application No. 07 74 4160.

* cited by examiner

WOUND DRESSING

This application is a U.S. national stage of International Application No. PCT/JP2007/060726 filed May 25, 2007.

TECHNICAL FIELD

The present invention relates to a wound dressing suitable for treating wounds, such as a burn, a bed sore, a sprain, a cut, an abrasion and an ulcer.

BACKGROUND ART

In recent years, it has turned out to be effective, for healing a wound, not to dry the wound surface but to keep it in a moist environment. In particular, since an ingredient contained in the exudate from a wound site is useful to promote the healing of a wound, a method in which a wound is not disinfected but treated in a moist environment created by the exudate from the wound site (hereafter may be called "moist healing") has turned out to be effective. Therefore, various kinds of wound dressings applicable to such a therapeutic method have been developed.

In order to perform a moist healing effectively, it is important that a moderate moist environment is maintained at a wound surface by the exudate from a wound site. Therefore, it is needed that a wound dressing has a function of moderately holding exudate on a wound surface instead of rapidly absorbing it. However, the moist healing allows a closed area to be formed on the wound surface since a wound dressing is firmly fixed to the skin in order to maintain a moist environment. As a result, when additional exudate oozes and is superfluously retained, the wound surface is compressed by exudate, leading to an "undermining" (a phenomenon in which the skin is hollowed by the pressure of exudate at a wound site). For this reason, it is also needed that the wound dressing has a function of moderately discharging exudate from on the wound surface.

In addition, if the material in contact with a wound site does not have breathability and sticks tight to the wound surface, removing the wound dressing can damage the healed or healing wound again. Therefore, it is also needed that the wound dressing does not stick tight to a wound surface.

As a conventional wound dressing, for example, JP-A-7-80020 discloses a dressing utilizing a porous film containing a dispersed hydrophilic substance or being coated with a hydrophilic substance. However, in this wound dressing, only the exudate-discharging function is improved by utilizing a hydrophilic porous film, and the objective of moderately holding exudate on a wound surface is not achieved.

Also, JP-A-10-151184 discloses a wound dressing applied onto an ulcer surface, which is formed of cotton, knitted or woven fabric, nonwoven, etc. containing chitin-chitosan cellulose mixed fibers, with a hydrocolloid agent applied thereto if desired. However, in the wound dressing, emphasis is placed on the function to absorb exudate, and the function to moderately hold exudate on a wound surface is insufficient. Further, it has been pointed out that a prolonged direct contact of the skin with the hydrocolloid agent of the wound dressing will cause a skin redness or a heat rash.

In order to solve the problems of conventional wound dressings set forth above, the inventor has developed a wound dressing having a sheet material that exerts an initial water pressure resistance as a permeable layer in contact with a wound site, and already applied for an international patent on it (see WO 2005/000372). The wound dressing has outstanding functions for use in a method to treat a wound while maintaining a moist environment created by the exudate from the wound site.

DISCLOSURE OF THE INVENTION

Problems to be Solved by the Invention

An objective of the present invention is to provide a further improved wound dressing suitable for a method to treat a wound while maintaining a moist environment created by exudate from the wound site.

Means for Solving the Problems

Namely, the present invention relates to:

(1) a wound dressing comprising at least three layers including a first layer, a second layer and a third layer in order from a side used in contact with a wound site, the layers being integrally stacked together, the first layer comprising a resin sheet material having a number of pores penetrating in a thickness direction, the second layer comprising a sheet material of which the surface is water-repellent and becomes water-permeable when pressure is applied, and the third layer comprising a sheet material capable of absorbing and holding water;

(2) the wound dressing according to the above-mentioned (1) further comprising a fourth layer comprising a resin film, a fabric or a nonwoven, in addition to the first layer, the second layer and the third layer, the layers being integrally stacked together;

(3) the wound dressing according to the above-mentioned (1) or (2), wherein the sheet material of the first layer is a polyolefin resin;

(4) the wound dressing according to any one of the above-mentioned (1) to (3), wherein the thickness of the sheet material of the first layer is 100 to 2000 μm, the opening of the pore on the surface used in contact with a wound site is 280 to 1400 μm in equivalent diameter, the opening of the pore on the other surface is smaller than that on the surface used in contact with a wound surface, and the density of such pores is 50 to 400/cm$^2$;

(5) the wound dressing according to any one of the above-mentioned (1) to (4), wherein the sheet material of the second layer is a polyolefin resin, the air permeability measured according to JIS-L-1096 is 5 to 2000 cm$^3$/cm$^2$·s, and the water repellency measured according to JIS-L-1092 is grade 3 or higher;

(6) the wound dressing according to any one of the above-mentioned (1) to (5), wherein the sheet material of the third layer is an airlaid nonwoven;

(7) the wound dressing according to any one of the above-mentioned (2) to (6), wherein the areas of the first to the third layers are almost the same, the area of the fourth layer, which covers the first to the third layers, is larger than each area of the first to the third layers, the fourth layer has an adhesive layer on at least a part of a non-stacked surface on the side having the stacked first to the third layers, and at least a part around the periphery of the first to the third layers does not have the adhesive layer or the fourth layer;

(8) the wound dressing according to any one of the above-mentioned (2) to (6), wherein the areas of the first to the third layers are almost the same, the area of the fourth layer, which covers the first to the third layers, is larger than each area of the first to the third layers, the fourth layer has an adhesive layer on at least a part of a non-stacked surface on the side having the stacked first to the third layers, and the fourth layer has a slit or a small pore along at least a part of the periphery of the first to the third layers; and (9) a method for manufacturing the wound dressing according to any one of the above-mentioned (1) to (8), comprising the step of non-fully applying a hot-melt adhesive to the sheet material of the second layer, followed by stacking the first layer sheet material onto the applied surface to join both layers.

Effect of the Invention

In order to be applied to a method for treating a wound in a moist environment created by the exudate from the wound, the wound dressing of the present invention can maintain a moist environment at a site where exudate oozes from a wound by not sucking up the exudate promptly while it can hold the exudate to prevent it from spreading over a larger area. Accordingly, therapeutic effect can be enhanced by holding exudate in an area near the wound site while unnecessary spread of the exudate, which causes irritation of the normal skin without a wound, can be prevented.

Therefore, the wound dressing of the present invention is suitable for the treatment of various kinds of wounds and most suitable for prevention and treatment of a bed sore in particular.

DESCRIPTION OF REFERENCE NUMERALS

1. First Layer
2. Second Layer
3. Third Layer
4. Fourth Layer
5. Wound Dressing
6. Adhesive Layer
7. Nonadhesive Area
8. Slit
11. Penetration Pore
12. Depressed Portion
13. Exudate
21. Second Sheet Material
22. Hot-Melt Adhesive
23. Adhesive Discharge Nozzle

BEST MODE FOR CARRYING OUT THE INVENTION

The wound dressing of the present invention is a dressing to stick onto a wound site, and can be applied in a method in which a wound is treated in a moist environment created by the exudate from the wound site. In the present invention, the "wound" widely means a skin injury including a burn, a bed sore, a sprain, a cut, an abrasion, an ulcer, an operative wound, and the like.

Hereinafter, the wound dressing configuration of the present invention will be described referring to drawings as needed.

The wound dressing of the present invention is a wound dressing comprising at least three layers including a first layer, a second layer and a third layer in order from a side used in contact with a wound site, wherein the layers are integrally stacked together. The wound dressing of the present invention may be a wound dressing comprising a fourth layer if desired in addition to the first layer, the second layer and the third layer, wherein the four layers are integrally stacked together.

Figure 1:
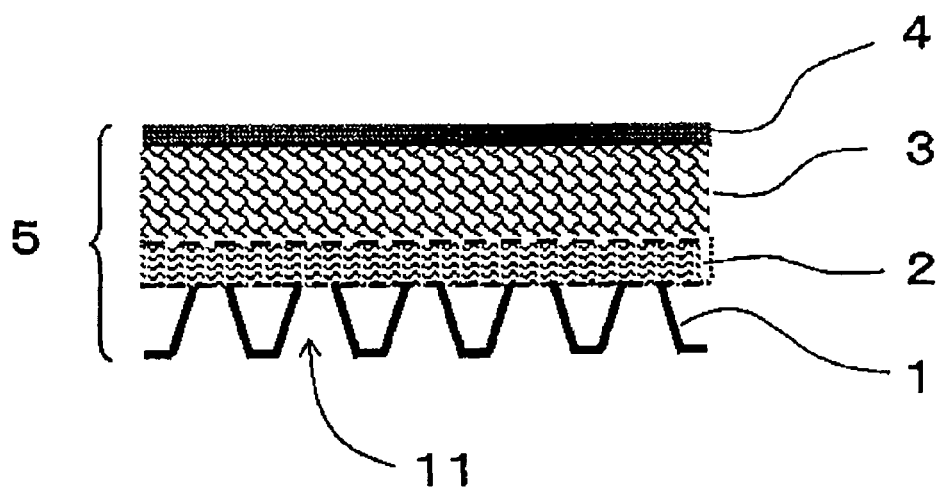
FIG. 1 is an enlarged segmentary schematic view (sectional view) illustrating the wound dressing of the present invention.

FIG. 1 is a schematic sectional view showing a preferable example of the present invention, including a fourth layer (4). When used, the first layer (1) is in contact with a wound site.

In the wound dressing of the present invention, the "layers are integrally stacked together" means the stacked condition created by at least partially joining each layer to the next and maintained without separation of any layer in normal use, unless any external force is applied to forcibly separate layers.

Examples of the joining means for stacking include, for example, fusion by heat sealing, and embossing, in addition to adhesion using adhesives such as a hot-melt adhesive, but are not limited thereto.

Hereinafter, each layer will be described in detail.

First Layer

The first layer is mainly intended to, at a site where exudate oozes from a wound, hold the exudate to prevent it from spreading over a larger area while maintaining a moist environment by not sucking up the exudate promptly. For healing of a wound, exudate held in an area near the wound site is sufficient, and it is not preferred that the exudate spreads beyond the area around the wound site. This is because, in such an area with spread exudate, the wound site may newly be expanded by, for example, irritation of the normal skin without a wound, slowing down the healing. Therefore, the present invention comprises the first layer intended for preventing the area covered with exudate from greatly spreading, thereby accelerating the healing of a wound.

The sheet material which composes the first layer (hereafter may be called "the first sheet material") is a resin sheet material.

In the present invention, the "sheet material" widely means both porous and nonporous sheet materials including, for example, a resin film, a fabric, a nonwoven, a net, and the like, and it is not particularly limited by the thickness thereof.

The first sheet material has a number of pores penetrating in the thickness direction (hereafter may be simply called "penetration pores"). Each of these pores is preferably independent, and the first sheet material preferably does not have any path inside through which water can flow in the in-plane direction. Since the first sheet material has a number of penetration pores, strong sticking to a wound site can be prevented.

Figure 2:
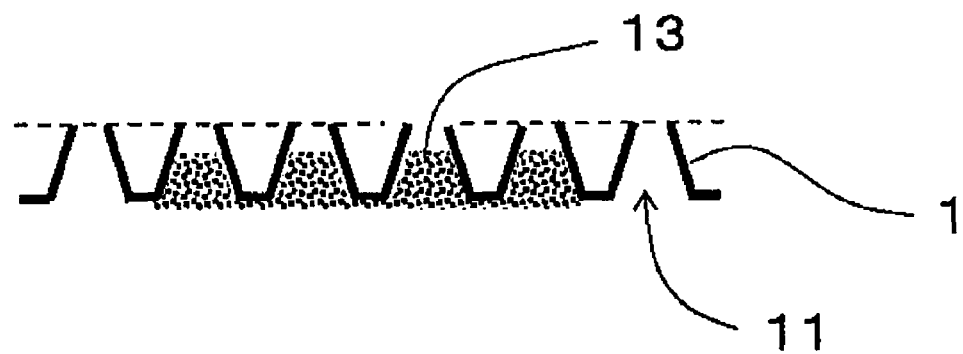
FIG. 2 is an enlarged segmentary schematic view (sectional view) illustrating a condition where exudate is caught by the first layer in the wound dressing of the present invention.

The penetration pore may be various in shape such as cylindrical, barrel shape, hand drum shape, etc., and preferably a tapered penetration pore of which the diameter is getting smaller in the thickness direction of the first sheet material toward the second layer (hereinafter, the tapered penetration pore of which the diameter is getting smaller toward the second layer like this may be called "the tapered pore"). FIG. 1 and FIG. 2 show examples where penetration pores are tapered pores.

The penetration pore opening on the surface of the first sheet material, the surface used in contact with a wound site (hereinafter may be called "the wound-side surface"), is preferably 280 to 1400 µm in equivalent diameter. The pore smaller than 280 µm in diameter is not preferable because the exudate tends to be prevented from passing through toward the second layer. On the other hand, larger than 1400 µm in diameter is not preferable because the second layer may contact with the skin of the wound site, causing difficulties in removing the wound dressing from the wound site or securing moderate retaining space for the exudate. The above "equivalent diameter" in the case when the shape of the opening is circular means the diameter thereof, and that in the case when the shape is not circular means the diameter of the circle equal in area to the opening.

When the penetration pore is a tapered pore, the diameter of the opening on the wound-side surface is, as described above, larger than that on the other surface, i.e., the second-layer-side surface, preferably 1.1 to 1.8 times larger, and more preferably 1.2 to 1.5 times larger.

As shown in FIGS. 1 and 2 for example, when the first sheet material has uneven surfaces, on the assumption of a plane in contact with the first sheet material on the wound side, the diameter of the pore at the position in contact with the plane is defined as the diameter of the opening on the wound-side surface. Similarly, on the assumption of a plane in contact with the first sheet material on the second-layer side, the diameter of the pore at the position in contact with the plane is defined as the diameter of the opening on the second-layer-side surface.

The penetration pore density is preferably 50 to 400 pores/cm$^2$, and preferably 60 to 325 pores/cm$^2$. Also, the ratio of pore openings to the entire wound-side surface of the first sheet material is preferably 15 to 60%.

The depth of the penetration pore is preferably about 100 to 2000 µm, and more preferably about 250 to 500 µm.

It is advantageous that the density, pore opening ratio and depth of the penetration pore are within the above-mentioned preferable range in terms of retaining moderate exudate on the wound surface by forming a moderate retaining space between the wound surface and the second layer, and preventing the exudate from spreading toward the in-plane direction.

The capacity of the above-mentioned retaining space is preferably 0.015 to 0.55 µL per penetration pore, more preferably 0.030 to 0.45 µL per penetration pore, and most preferably 0.040 to 0.35 µL per penetration pore. The capacity of the retaining space less than 0.015 µL per penetration pore is not preferable because such a retaining space tends to make it difficult not only to hold exudate on the wound surface but also to prevent the exudate from spreading in the in-plane direction. On the other hand, more than 0.55 µL per penetration pore is not preferable because the rate of exudate absorption by the second layer is increased and it tends to become difficult to maintain a moderate moist environment created by the exudate from the wound site.

The first sheet material is preferably a resin film, and specifically, a porous film made by punching a resin film is more preferable. The resin which forms the first sheet material is preferably a polyolefin resin, and polyethylene resin is especially preferred. Consequently, the first sheet material is preferably a porous polyolefin resin film, and a porous polyethylene resin film is especially preferred.

The first sheet material may be hydrophilic or hydrophobic, but the surface thereof is preferably hydrophobic. When the material is a polyolefin resin, the surface can be hydrophobic. Having hydrophobic property is advantageous in preventing tight sticking to a wound site.

The first sheet material preferably has a property of becoming water-permeable when pressure is applied. In the present invention, "become water-permeable when pressure is applied" means that applying a hydraulic pressure higher than a predetermined level on the sheet allows water to permeate through the sheet. Hereinafter, "the property of becoming water-permeable when pressure is applied" may be called "initial water pressure resistance".

The initial water pressure resistance of the first layer may be relatively low, and preferably lower than that of the second layer described below. "Initial water pressure resistance is low" means that a relatively low hydraulic pressure allows water to permeate.

The initial water pressure resistance of the first sheet material can easily be realized when the surface of the first sheet material is hydrophobic and when the penetration pore is a tapered pore. Also, the initial water pressure resistance of the first sheet material can easily be realized when the penetration pore density is 50 to 400 pores/cm$^2$ and when the pore opening ratio is 15 to 60%. As used herein, "the initial water pressure resistance of the first sheet material" means the initial water pressure resistance against the pressure from the side in contact with the wound site.

The first sheet material having initial water pressure resistance lets water permeate through the above-mentioned penetration pores when pressure is applied. Consequently, it is preferred that the first sheet material substantially does not allow water to permeate through any part other than penetration pores.

The fact that the first sheet material has initial water pressure resistance can be confirmed, for example, by the following method. Namely, when the first sheet material is held in a horizontal position in the air at a certain height by the use of a metal frame etc. and water is gradually dropped down onto the same part of the sheet material with a pipet, if the sheet has initial water resistance, the water initially does not drop through the sheet material, but as the amount of dropped water increases, the water comes to drop through the sheet material.

The first sheet material works to prevent the exudate oozing from a wound from spreading in the in-plane direction. In an early stage of oozing of the exudate from a wound, i.e., shortly after the application of the wound dressing of the present invention onto a wound surface, exudate permeates halfway through the above-mentioned penetration pores, as shown in FIG. 2. Therefore, the exudate is caught in the penetration pores, being prevented from moving in the in-plane direction, and thereby is held between the wound surface and the first layer without spreading beyond the area of the wound site, to maintain a moist environment. In order to effectively maintain a moist environment by preventing the great spread of the exudate, it is advantageous that the first sheet material has initial water pressure resistance, that the penetration pores are tapered pores, and that the capacity of the above-mentioned retaining space is 0.015 to 0.55 μL per penetration pore.

In the following stage, the exudate further oozing out increases its pressure, permeates through the first layer, reaches the surface of the second layer, and then further permeates toward the third layer. It is preferred that the exudate does not return through the first layer. In particular, the exudate having penetrated through the second layer can cause infection if it is returned to the wound site by, for example, the compression of the wound dressing by an external force, because a long period of time has passed since the exudate oozed and there is a risk of propagation of various germs. In preventing such return of the exudate, it is advantageous that the penetration pore is a tapered pore.

Figure 3:
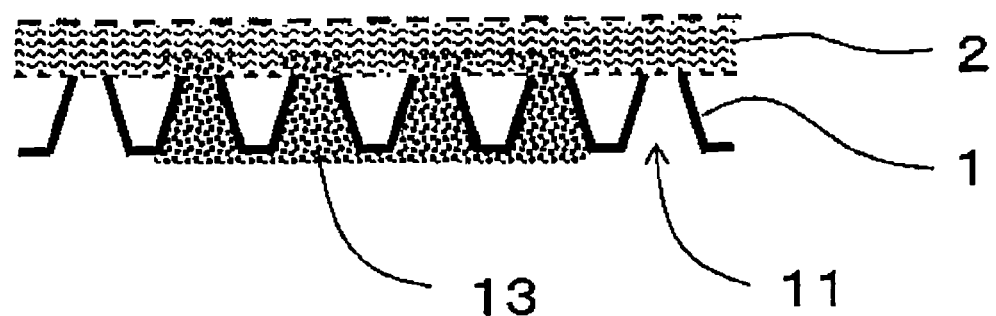
FIG. 3 is an enlarged segmentary schematic view (sectional view) illustrating a condition where exudate is caught by the first layer in the wound dressing of the present invention.

The first layer and the second layer are preferably in close contact with each other. Specifically, they are preferably in close contact to the extent that the exudate can not spread in the in-plane direction at the interface between the first layer and the second layer even when the above-mentioned retaining space is filled with the exudate, as shown in FIG. 3. Such close contact can be realized by non-fully applying, as described below, a hot-melt adhesive to the surface of the second layer and joining the two layers.

Figure 4:
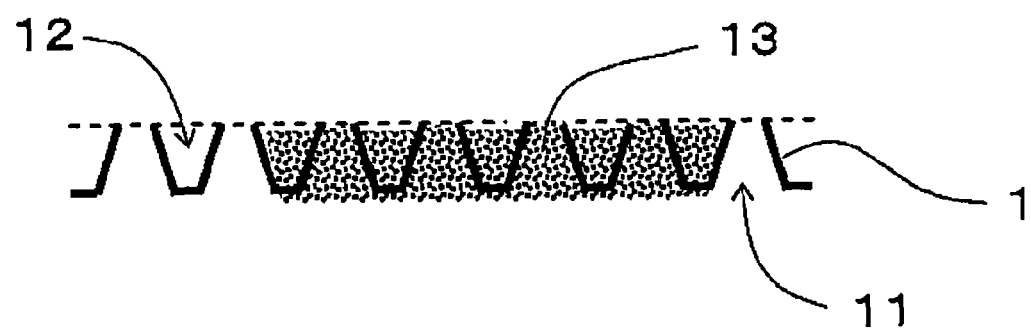
FIG. 4 is an enlarged segmentary schematic view (sectional view) illustrating a condition where exudate is caught by the first layer in the wound dressing of the present invention.

Regardless of the quality of the above-mentioned close contact, using the first sheet material having tapered pores and uneven surface, as shown in FIGS. 1 and 2 for example, is still more advantageous in preventing the exudate from spreading in the in-plane direction because the exudate which has reached the surface of the second layer can be caught in the depressed portions as shown in FIG. 4.

Second Layer

The second layer has initial water pressure resistance, the property of becoming water-permeable when pressure is applied. Since the second layer has initial water pressure resistance, the wound dressing of the present invention has, in practical use, a function to withstand the pressure by the exudate oozing from a wound and prevent the exudate from permeating in an early stage of exudate oozing, and allow the exudate to permeate when the pressure by the exudate exceeds a predetermined level.

The sheet material which composes the second layer (hereafter may be called "the second sheet material") is a sheet material having initial water pressure resistance. Since the initial water pressure resistance can easily be realized when the surface is water-repellent, it is preferable that second layer is composed of a sheet material having a water-repellent surface and initial water pressure resistance.

In the present invention, as indexes of the initial water pressure resistance, air permeability (according to JIS-L-1096) and water repellency (according to JIS-L-1092) can be used. The second sheet material preferably has a permeability within the range of 5 to 2000 $(cm^3/cm^2 \cdot s)$ and a water repellency of grade 3 or higher. The initial water pressure resistance suitable for the purpose of the present invention can be realized when the air permeability and the water repellency are within the above ranges, and therefore a moderate moist environment which enhances the healing effect can be realized by preventing permeation and absorption of exudate in the early stage with less exudate and by allowing permeation and absorption of excessive exudate in the stage with excessively oozed exudate. The air permeability is more preferably within the range of 15 to 500 $(cm^3/cm^2 \cdot s)$, with which a moderate moist environment presumably can be maintained for a long period of time.

The above-mentioned air permeability less than 5 $(cm^3/cm^2 \cdot s)$ is not preferable because, in this case, the water pressure resistance of the second sheet material is so high that the exudate cannot permeate into the third layer even under excessive pressure because of increased amount of exudate in the closed area on the wound surface, and therefore there is a risk that the exudate returns to the wound surface side or spreads in the in-plane direction. On the other hand, the air permeability more than 2000 $(cm^3/cm^2 \cdot s)$ is not preferable because, in this case, the water pressure resistance of the second sheet material is so low that the exudate is absorbed promptly, and therefore there is a risk of being unable to maintain a moderate moist environment.

Also, the water repellency lower than grade 3 (grade 2 or lower) is not preferable because, in this case, the water pressure resistance is so low that the exudate is absorbed promptly, and therefore there is a risk of being unable to maintain a moderate moist environment.

The above air permeability is determined according to the method A (Frazier type method) described in 8.27.1 of JIS-L-1096. In the measuring method, a Frazier type air permeability tester for textiles is used. Specifically, air permeability is determined by attaching a specimen onto the Frazier type tester, adjusting the induced draft fan with a rheostat so that the differential barometer reads 125 Pa, and then calculating the amount of air $(cm^3/cm^2 \cdot s)$ passing through the specimen from the pressure shown by the vertical barometer at the time and the kind of orifice used, using the table attached to the tester. The air permeability is obtained by calculating the arithmetic mean of 5 measurements.

Meanwhile, the water repellency is determined according to the water repellency test (spray test) described in 6.2 of JIS-L-1092. In the measuring method, a water repellency test apparatus with a spray nozzle having predetermined capability (the ability to spray 250 mL of water for 25 to 30 s) is used. Specifically, water repellency is determined by (1) attaching a specimen (about 20 cm×20 cm) onto the specimen holding frame of the water repellency test equipment, and spraying 250 mL of water from the spray nozzle onto the specimen over 25 to 30 s, (2) removing the holding frame from the stand of the water repellency test apparatus, and performing predetermined operation to let excessive water drops fall off the specimen, and (3) comparing the wet condition of the specimen attached to the holding frame with the comparison samples in predetermined wet conditions to grade the specimen. The predetermined operation in the above (2) means an operation of, while holding one side of the above holding frame to keep the specimen face down in a horizontal position, hitting the opposite side against something hard, and then rotate it 180° to do the same operation.

In the water repellency test, the temperature is set to 20±2° C., and as the water for this test, distilled water is used.

The comparison samples in wet condition are as follows.

Grade 1: The entire surface is wet

Grade 2: Half of the surface is wet and small separate waterdrops penetrate the fabric Grade 3: The surface is wet with small separate waterdrops on the surface Grade 4: The surface is not wet but small waterdrops are on the surface Grade 5: No wetting and no waterdrops are on the surface Accordingly, "water repellency is grade 3 or higher" includes "The surface is wet with small separate waterdrops on the surface", "the surface is not wet but small waterdrops are on the surface" and "no wetting and no waterdrops are on the surface", and excludes "the entire surface is wet" and "half of the surface is wet and small separate waterdrops penetrate the fabric" in the water repellency test.

The above water repellency test of JIS-L-1092 is a similar test method to ISO4920.

The second sheet material may be a nonwoven, or a porous film or fabric, which is formed of a hydrophobic material such as a polyolefin resin (for example, polypropylene, polyethylene, etc.), a polyester resin (for example, polyethylene terephthalate, polybutylene terephthalate, polypropylene terephthalate, etc.), polyamide resin (for example, nylon 6, nylon 66, etc.) or polyurethane resin. The second sheet material is preferably a nonwoven, more preferably a nonwoven comprising polyolefin fibers, and most preferably a nonwoven comprising polypropylene fibers.

The kind of the nonwoven is not particularly limited, and various kinds of wetlaid or drylaid type nonwovens, for example, thermalbonded nonwovens, needlepunched nonwovens, spunlaced nonwovens, spunbonded nonwovens, meltblown nonwovens, flashspun nonwovens, or complex nonwovens thereof (SMS, SMMS, etc.), etc. may be used.

Also, a water-repellent treated nonwoven which is formed of hydrophilic fibers such as cotton and rayon may also be used.

As the nonwoven used for the second sheet material, particularly preferred are a meltblown nonwoven and a flashspun nonwoven obtained by meltblowing and flashspinning, respectively.

The meltblown nonwoven and the flashspun nonwoven are formed of, for example, superfine fibers with fiber diameter of about 20 μm or less. Therefore, as for the meltblown nonwoven and the flashspun nonwoven, a fabric with desired initial water resistance pressure can be obtained easily because interfiber voids thereof can be smaller, compared to those of nonwovens obtained by other manufacturing methods such as the spunbonding method, when fiber area weight (basis weight) of both are the same.

Simply stated, the meltblown nonwoven is a fabric which is formed of continuous superfine fibers, and is obtained by elongation and fibrillation of fibers while blowing high-temperature and high-pressure air to the outlet of a spinning nozzle. The meltblown nonwoven may be used as what is called an SMS nonwoven, an SMMS nonwoven, or the like, formed by stacking spunbonded and meltblown nonwovens in layers.

The flashspun nonwoven is a reticulated nonwoven which is formed of continuous superfine fibers, and is obtained by dissolving fiber forming polymer in a low-boiling solvent uniformly under high temperature and high pressure and then, while discharging the above solution from a nozzle, rapidly gasifying and expanding the solvent only in order to elongate and solidify the fiber forming polymer.

The nonwoven as the second sheet material may be calendered. The calendering as used herein means pressure processing of a nonwoven with calendering rollers or embossing rollers adjusted to a temperature below the melting point. The calendering thermally fuses part of the fibers forming the nonwoven and crushes interfiber voids, and therefore the nonwoven can easily acquire desired initial water resistance pressure.

Third Layer

The third layer is a layer for absorbing the exudate which oozes out from the wound site, penetrates through the first layer, and then through the second layer. For that reason, the third layer is composed of a sheet material capable of absorbing and holding water. It is because a sheet material capable of absorbing and holding water is capable of absorbing and holding exudate.

"Capable of absorbing and holding water" means that when placed in contact with liquid water, the sheet naturally absorbs the water and holds at least some of the water in its voids against gravitational force. Therefore, when the sheet material holding absorbed water is lifted, if part of the absorbed water is still held without falling, it can be said that the sheet material is capable of absorbing and holding water. Preferably, the sheet material is capable of absorbing water via capillarity action.

A sheet material capable of absorbing and holding water used as the sheet material which composes the third layer (hereafter may be called "the third sheet material") may be a sponge-like sheet material, and preferably is a sheet material formed of hydrophilic fibers such as cotton, or hydrophilically treated fibers. The third sheet material is preferably a hydrophilically treated nonwoven, fluff pulp, an airlaid nonwoven, or the like.

When the third sheet material is formed of fibers, it is preferred that interfiber adhesion by a binder (adhesive) or compression is performed to bind fibers together to the extent that neither waste fibers nor other minor materials drop off from a cut end when the wound dressing is cut. Consequently, it is also preferred that fibers with thermal adhesiveness are at least partly used.

The third sheet material is particularly preferably an airlaid nonwoven. An airlaid nonwoven is a nonwoven obtained by cutting and dispersing raw material pulp fibers or short fibers uniformly into the air, and having them deposited on a revolving porous cylinder or a movable screen belt while spraying a water-soluble adhesive thereon for interfiber bonding. To have the exudate easily absorbed, it is particularly preferred to use a pulp-fiber-based nonwoven. As a manufacturing method of these nonwovens, the DAN-WEB method, the Honshu method, or the like may be used.

The airlaid nonwoven preferably contains synthetic fibers with little strength deterioration in wet conditions, specifically synthetic fibers such as polyamide including nylon 6 and nylon 66, polyester including polyethylene terephthalate, polyethylene and polypropylene.

The airlaid nonwoven may contain binder fibers. A binder fiber is a fiber expressing adhesive property by entirely or partially changing its state through fusion and solidification depending on temperature conditions. Specific examples of the binder fibers include completely fusible fibers containing a single low-melting-point resin such as a polyester resin and a polyamide resin, or a polyolefin resin; core-in-sheath composite fibers containing two resins having different melting points such as polyethylene resin/polypropylene resin or low-melting-point polyester resin/polypropylene resin; and side-by-side composite fibers.

The third sheet material may contain absorption materials such as high-absorbent resin powder to increase the ability to absorb and hold exudate. Since components of an airlaid nonwoven such as fibers are pressure-bonded with each other with a binder, even if the wound dressing is cut before use, the high-absorbent resin powder, fluff pulp, etc. does not easily drop off. The absorption material means a material which, when placed in contact with a liquid, absorbs the liquid, swells and gelates in a short period of time. As the absorption material, preferably used are polyacrylic, starch-based, carboxymethylcellulose-based, polyvinyl alcoholic or polyethylene oxide-based so-called super absorbent polymers (SAP); high-absorbent natural polysaccharide such as alginic acid, dextran, etc.; and the like. The absorption material may be in the form of fiber, as well as powder and granule. In addition, by treating the absorption material with a calcium salt, a hemostatic effect in the wound surface can be provided.

The fiber forming the third sheet material may be a super water-absorbent fiber which itself has water absorbability equivalent to that of the above super absorbent polymer (SAP), and virtually, the third sheet material may be formed of only super water-absorbent fibers. In the third sheet material virtually formed of only super water-absorbent fibers, even when the wound dressing is cut before use, the fibers are immune from dropping off, compared with the case where powder high-absorbent resin is used. In the case where powder resin is used, as the powder resin absorbs exudate and swells while in use, the third sheet material can become uneven, and the layers of the wound dressing may easily separate. However, the third sheet material virtually formed of only super water-absorbent fibers is unlikely to become uneven, and therefore the separation of layers can be prevented. Specific examples of the super water-absorbent fibers include, for example, "Lanseall (trademark) F" by Toyobo Co., Ltd.

When an airlaid nonwoven as the third layer absorbs exudate, the hydrogen bond between pulp fibers in the airlaid nonwoven is broken and water-soluble binder is dissolved, resulting in reduction of interfiber binding in wet conditions. In particular, when the airlaid nonwoven contains a super water-absorbent resin, the strength of the resin reduces because of gelation, and the gelation increases the resin in volume, resulting in physical break of the entanglement and binding between fibers. Thus the wet strength of the airlaid nonwoven may significantly decline. However, an airlaid nonwoven can retain minimum interfiber binding by containing water-insoluble long fibers and binder fibers; thereby the wet strength reduction of the airlaid nonwoven can be controlled. Therefore, the separation or disintegration of the third layer of the wound dressing due to the strength reduction of the airlaid nonwoven, which often occurs after exudate absorption, can be controlled, thereby the wound dressing can be removed from the wound surface easily and beautifully.

The airlaid nonwoven as the third layer may be softened by perforation. The "perforation" as used herein means a process of making many pores in a nonwoven. As fibers in an airlaid nonwoven are bound each other with an adhesive and the stiffness of the fabric is high, and therefore its flexibility may be impaired. However, since the above perforation can soften the airlaid nonwoven, the wound dressing can thereby be made flexible so as to fit the skin. Also, since perforation allows the nonwoven to absorb exudate through the pores as well, once the nonwoven starts absorbing exudate, the rate of absorption will be increasingly high.

The cross-section shape of the pore generated by perforation is not particularly limited. The pore may completely penetrate or not penetrate the airlaid nonwoven.

The third sheet material may be a complex sheet. The complex sheet can be obtained by, for example, impregnation of a nonwoven with an acrylic acid monomer followed by polymerization and crosslinking reaction. Another example of the complex sheet can be obtained by flow casting, where a dispersion liquid containing a fibrous material having high hydration reactivity (for example, microfibril etc.) and a water swellable solid substance (for example, various kinds of polysaccharide, a flocculent, super absorbent polymer (SAP), etc.) dispersed in a mixed solvent of an organic catalyst and water, is poured into a support sheet such as a nonwoven, followed by drying off the dispersion liquid.

The third sheet material may be given a stretch property by incisions made in an irregular way, for example, by pores generated by perforation etc.

The thickness of the third sheet material is not particularly limited, but considering the capacity to absorb exudate, about 0.4 to 0.8 mm is preferred. The area weight of the third sheet material is preferably 60 to 170 g/m².

Fourth Layer

The wound dressing of the present invention comprises the first to the third layers, and if desired, further comprises a fourth layer (4) as shown in FIG. 1, for example. The fourth layer is provided in order to prevent the exudate absorbed by the third layer from moving outside. The wound dressing of the present invention does not always need to have the fourth layer. However, when not having the fourth layer, the third layer preferably has another sheet material in combination to prevent the exudate absorbed by the third layer from moving outside and soiling, for example, clothes or bedding.

The fourth layer is preferably a resin film, a fabric, a nonwoven, or a combination thereof. Among them, a resin film is particularly preferred as the fourth layer.

As the resin film, a resin film which prevents the penetration of a liquid is preferred. Examples of the resin film include a resin film formed of an olefin resin (polyethylene, polypropylene, etc.), polyester-resin, nylon resin, or the like. A stretch resin film formed of polyurethane resin etc. is also preferably used. The use of a stretch resin film improves the fit of the wound dressing to the skin. The thickness of the resin film is not particularly limited and may be suitably set in consideration of strength, flexibility, etc.

The use of a resin film which prevents the penetration of a liquid as the fourth layer is effective in preventing not only exudate from moving outside the wound dressing but also water and dirt a soil from entering externally. The use of a resin film as the fourth layer also enables more effective maintenance of a moist environment by preventing evaporation of exudate.

As described below, a slit etc. may be provided at a part of the resin film to prevent the penetration of a liquid, if needed. In this case, the slit can give passage for a liquid. Even in this case, however, liquid penetration is prevented at any part except the slit. Consequently, even in such an embodiment, the fact remains that the film is "a resin film which prevents the penetration of a liquid" unless otherwise noted."

The outer surface of the fourth layer may be colored or patterned if desired. For example, coloring the surface in a skin-like color makes it less conspicuous. Conversely, a conspicuous pattern, illustration, photograph printing, etc. may be intentionally given for fashionability and a playful spirit.

The fourth layer may be transparent. In this case, the condition of the exudate in internal layers is visible, and therefore, appropriate time for dressing replacement is easy to know.

The wound dressing of the present invention is in the form of a stacked sheet, and it may be supplied, for example, as a roll of a long sheet, which may be cut into a desired length before use. In this case, if the wound dressing has the fourth layer, the areas of the stacked first to the fourth layers are the same, and therefore, to fix the wound dressing to a wound surface, a medical tape etc. may be used.

Figure 5:
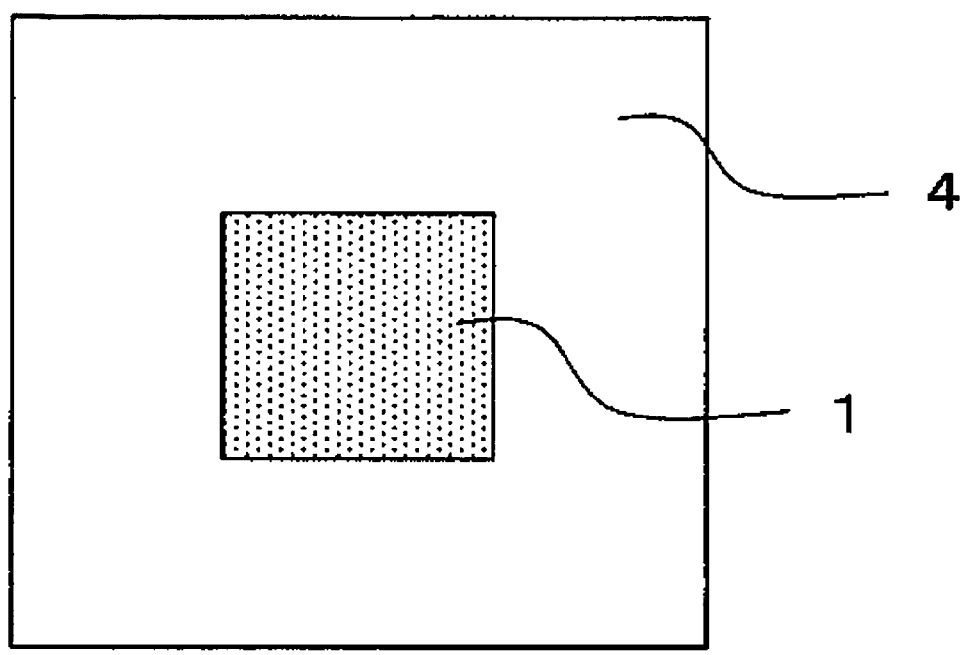
FIG. 5 is a schematic plan view of the wound dressing of the present invention.

The wound dressing of the present invention may be cut into an appropriate size before supplied. In the wound dressing in this case, preferably, the areas of the first to the third layers are almost the same, and the area of the fourth layer, which covers the first to the third layers, is larger than the area of the first to the third layers. In more detail, as shown in FIG. 5, for example, it is preferred that the first to the third layers are stacked in the same shape, and the fourth layer spreads beyond the periphery of the first to the third layers in whole or in part. FIG. 5 is a schematic plan view seen from the first layer side. In this example, the second layer and the third layer are hidden behind the first layer, and the fourth layer protrudes partly or in whole at the periphery.

In the above desirable embodiment in which the area of the fourth layer is larger, the fourth layer preferably has an adhesive layer on at least a part of a non-stacked surface (hereinafter, may be called "the exposed surface") on the side having the stacked first to the third layers (hereinafter, may be called "the inside" and the other side may be called "the outside"). This adhesive layer is provided in order to fix the wound dressing to the skin. Therefore, the adhesive layer is preferably an adhesive layer capable of fixing the wound dressing and being removed easily. In particular, an adhesive layer comprising a hypoallergenic adhesive not causing skin irritation when in contact with the skin, for example, an acrylic or silicon adhesive, is preferred, and an adhesive layer used for known adhesive plasters (example: "Band-Aid (trademark)") etc. can be adopted.

Figure 6:
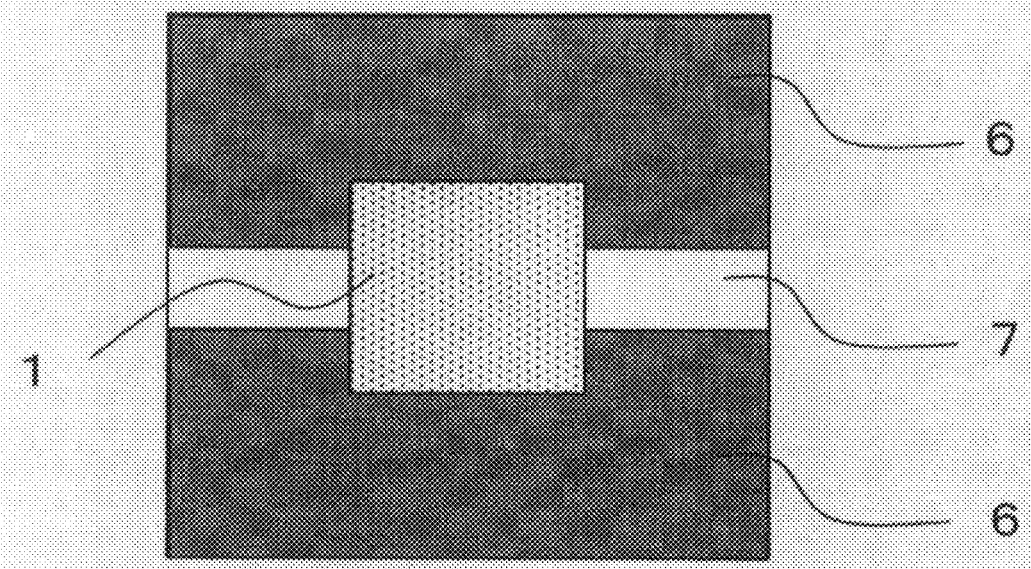
FIG. 6 is a schematic plan view of the wound dressing of the present invention.
Figure 7:
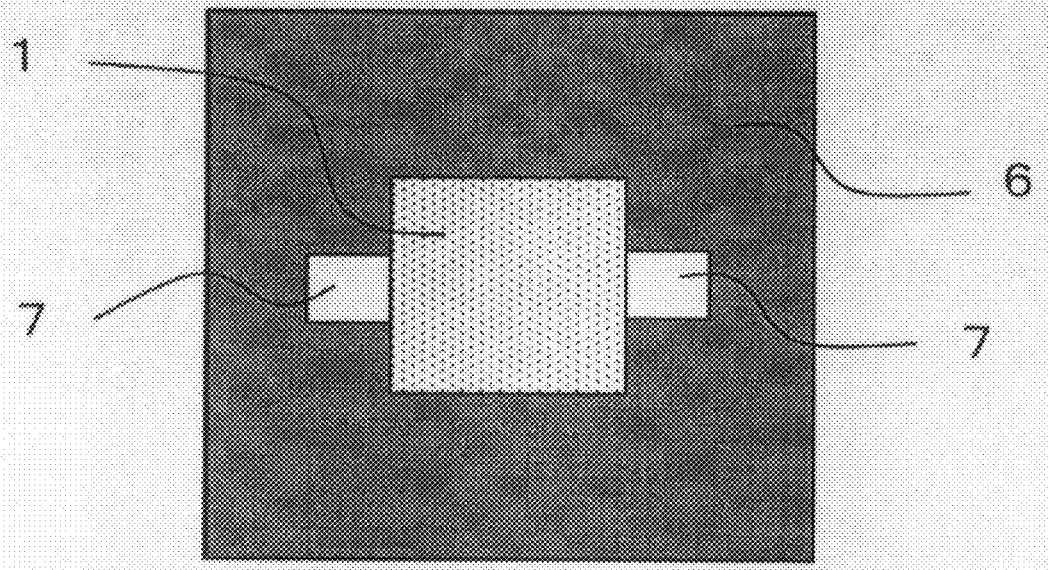
FIG. 7 is a schematic plan view of the wound dressing of the present invention.
Figure 8:
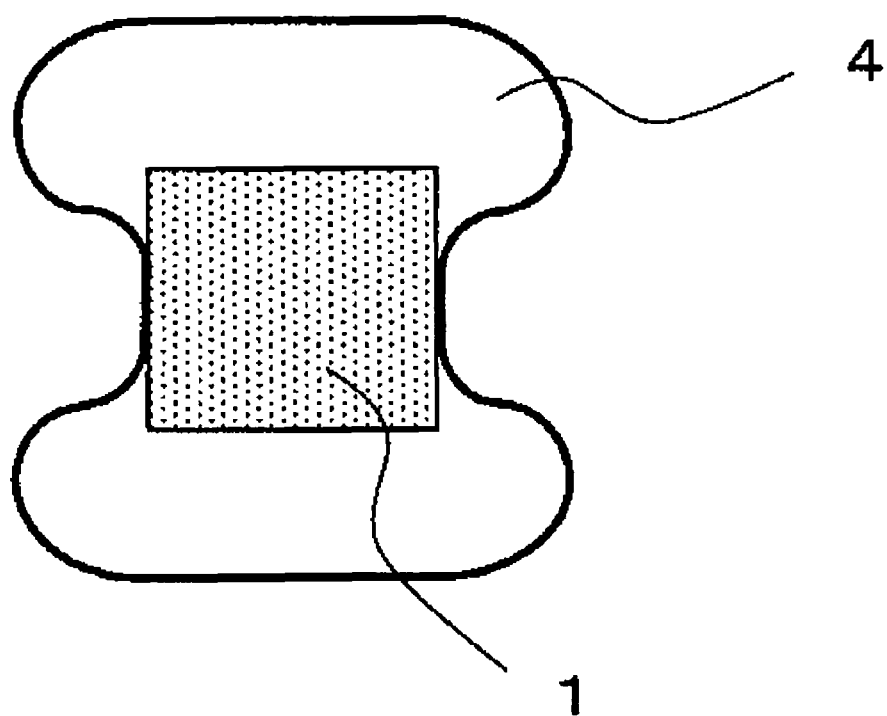
FIG. 8 is a schematic plan view of the wound dressing of the present invention.
Figure 9:
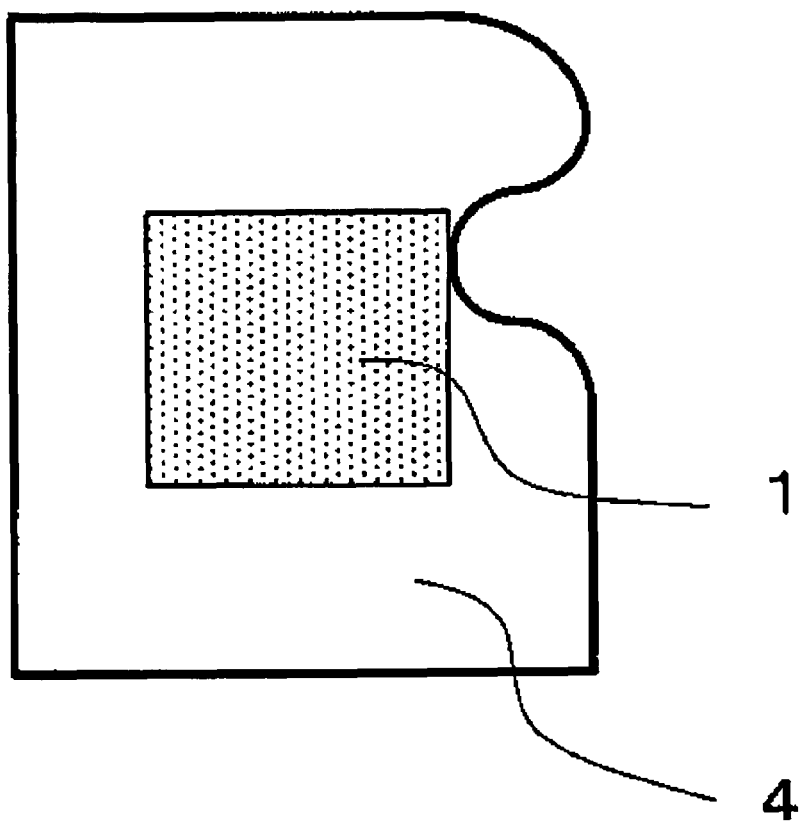
FIG. 9 is a schematic plan view of the wound dressing of the present invention.

In the above embodiment in which the fourth layer has an adhesive layer on at least a part of the inside exposed surface, further, embodiments not having the adhesive layer on at least a part around the periphery of the first to the third layers as shown in FIG. 6 and FIG. 7, and embodiments not having the fourth layer on at least a part around the periphery of the first to the third layers as shown in FIG. 8 and FIG. 9 are also preferred. The exposed surface of the fourth layer in FIG. 8 and FIG. 9 may have an adhesive layer. In these preferable embodiments, the part not having the adhesive layer or the part not having the fourth layer does not adhere to the skin, forming an open area. As a result, the open area allows air to be supplied to around the wound site, which successfully suppresses propagation of anaerobic bacteria and thereby prevents infection.

Among the embodiments not having the adhesive layer on at least a part around the periphery of the first to the third layers as shown in FIG. 6 and FIG. 7, the embodiment, as shown in FIG. 6, in which the part not having the adhesive layer (hereinafter may be called a "nonadhesive area") extends to the periphery of the fourth layer is preferred when the sheet material of the fourth layer is a poorly breathable sheet material (for example, a nonporous resin film) and has an adhesive layer. The purpose is to secure breathability through the peripheral part. On the other hand, the embodiment, as shown in FIG. 7, in which the nonadhesive area does not extend to the periphery of the fourth layer and the whole periphery has an adhesive layer is preferred when the sheet material of the fourth layer is a breathable sheet material (for example, a nonwoven) and has an adhesive layer. This is because the breathability of a breathable sheet material including a nonwoven etc. is blocked by the adhesive layer but is maintained at a nonadhesive area.

Figure 10:
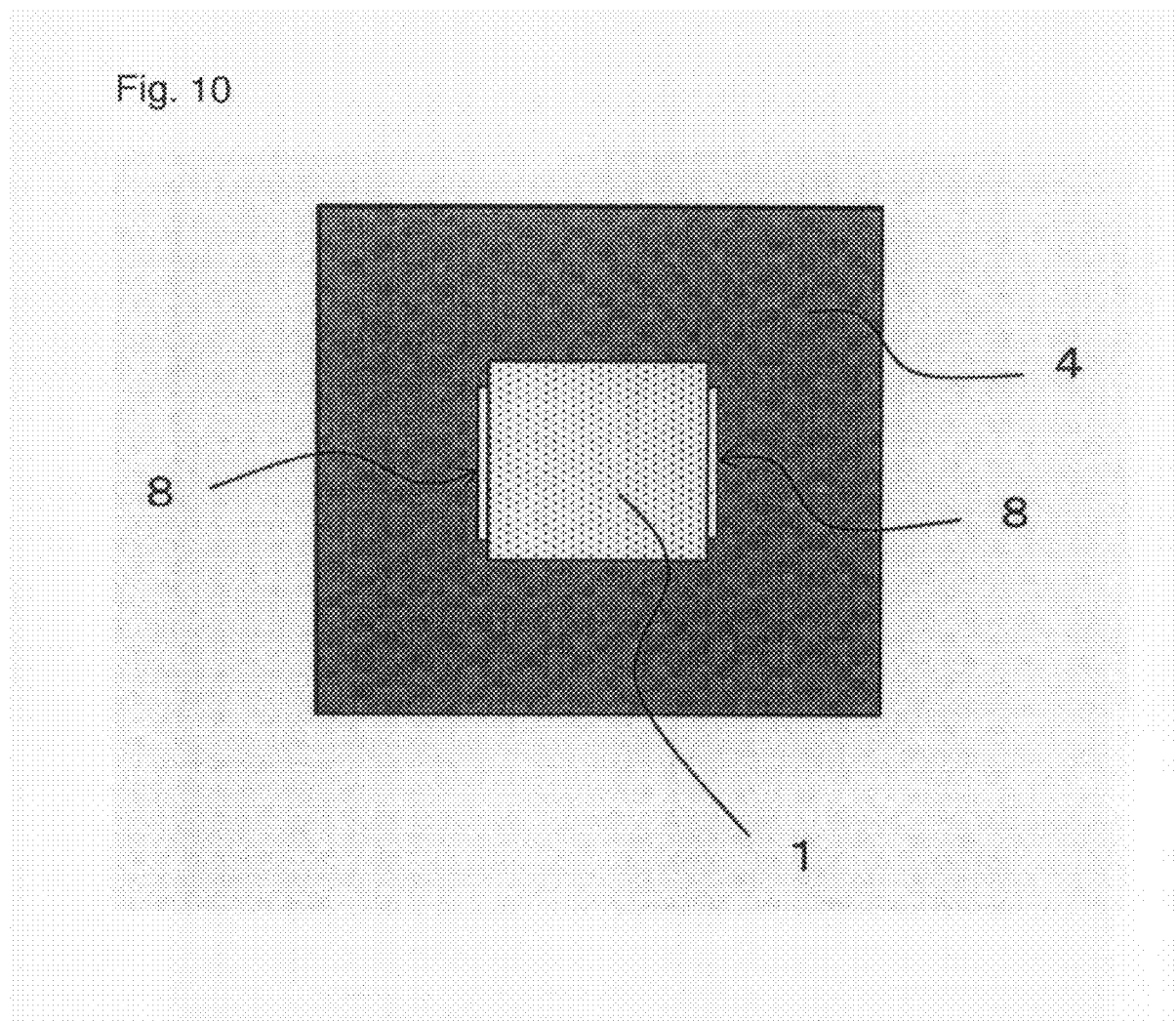
FIG. 10 is a schematic plan view of the wound dressing of the present invention.

As another embodiment in which an open area having the above effect is formed, as shown in FIG. 10, for example, the fourth layer may have a slit or a small pore along at least a part of the periphery of the first to the third layers. In FIG. 10, the exposed surface of the fourth layer may have an adhesive layer. The size and number of the slit or pores may be suitably determined taking the advantage of air supply and the disadvantage of exudate moving outside into consideration.

Providing another sheet material which covers and hides the slit or pore without blocking them is effective in preventing exudate from soiling clothes and bedding.

Manufacturing Method

The method for manufacturing the wound dressing of the present invention is not particularly limited so long as the first to the third layers or the first to the fourth layers can be integrally stacked and the object of the present invention is not hampered, and a publicly known method may be suitably adopted. Each layer may be integrally stacked at the same time; or after stacking and joining some layers, another layer may be stacked and joined for integration.

In manufacturing the wound dressing of the present invention, in order to join the first layer and the second layer, preferred is a step of non-fully applying a hot-melt adhesive to the surface of the second layer sheet material, followed by stacking the first layer sheet material onto the applied surface to join the both layers. In this preferred step, the hot melt adhesive is non-fully applied to the surface because application to the entire surface can block the exudate moving through the interface between the first layer and the second layer.

Figure 11:
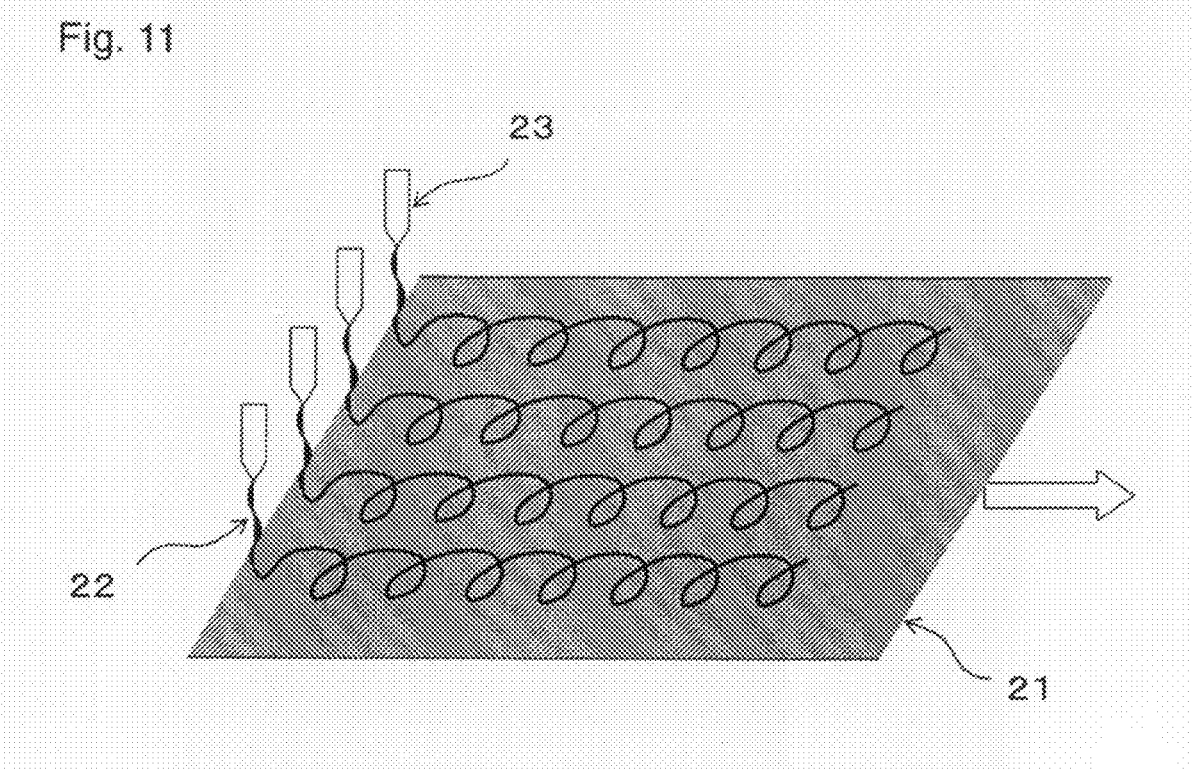
FIG. 11 is a schematic view (perspective view) illustrating the manufacturing process of the wound dressing of the present invention.

The "non-fully applying" means applying to generate applied parts and unapplied parts. The application pattern is not particularly limited, and various kinds of non-full application patterns may be adopted. Preferred is an application pattern where an applied part and an unapplied part alternately appear, for example, dot pattern, striped pattern, lattice pattern, or the like. Particularly preferred application pattern is a spiral application pattern, for example, as shown in FIG. 11. Since this pattern is easily realizable by, while feeding the second sheet material, discharging a hot-melt adhesive from a nozzle above to form a spiral pattern, excellent productivity and good joint condition can be provided.

The wound dressing of the present invention manufactured as described above can maintain a moist environment at a site where exudate oozes from a wound by not sucking up the exudate promptly while holding the exudate to prevent it from spreading over a larger area. Accordingly, therapeutic effect can be enhanced by holding exudate around the wound site while unnecessary spread of the exudate, which causes irritation of the intact normal skin, can be prevented.

The invention claimed is:

1. A wound dressing comprising at least three layers including a first layer, a second layer and a third layer in order from a side used in contact with a wound site, the layers being integrally stacked together, the first layer comprising a resin sheet material having a plurality of pores penetrating in a thickness direction,
wherein the thickness of the resin sheet material is 100 to 2000 μm,
wherein an opening of each pore on a surface used in contact with a wound site is 280 to 1400 μm in equivalent diameter,
wherein an opening of each pore on an opposite surface of the first layer is smaller than that on the surface used in contact with a wound site,
wherein the density of said pores is 50 to 400/cm$^2$,
wherein said surface used in contact with a wound site is hydrophobic,
wherein said first layer has an initial water pressure resistance, and
wherein the resin sheet material substantially does not allow water to permeate through any part other than said pores, the second layer comprising a sheet material having a water-repellent surface, said second layer has an initial water pressure resistance higher than that of the first layer, and the third layer comprising a sheet material capable of absorbing and holding water.

2. The wound dressing according to claim 1 further comprising a fourth layer comprising a resin film, a fabric or a nonwoven, in addition to the first layer, the second layer and the third layer, the layers being integrally stacked together.

3. The wound dressing according to claim 2, wherein
the areas of the first to the third layers are the same,
the area of the fourth layer, which covers the first to the third layers, is larger than each area of the first to the third layers,
the fourth layer has an adhesive layer on at least a part of a non-stacked surface on the side having the stacked first to the third layers, and
at least a part around the periphery of the first to the third layers does not have the adhesive layer or the fourth layer.

4. The wound dressing according to claim 2, wherein
the areas of the first to the third layers are the same,
the area of the fourth layer, which covers the first to the third layers, is larger than each area of the first to the third layers,
the fourth layer has an adhesive layer on at least a part of a non-stacked surface on the side having the stacked first to the third layers, and
the fourth layer has a slit or a small pore along at least a part of the periphery of the first to the third layers.

5. The wound dressing according to claim 1, wherein the sheet material of the first layer is a polyolefin resin.

6. The wound dressing according to claim 1, wherein
the sheet material of the second layer is a polyolefin resin,
the air permeability measured according to JIS-L-1096 is 5 to 2000 $cm^3/cm^2 \cdot s$, and
the water repellency measured according to JIS-L-1092 is grade 3 or higher.

7. The wound dressing according to claim 1, wherein the sheet material of the third layer is an airlaid nonwoven.

8. The wound dressing according to claim 1, wherein the capacity of the retaining space between the wound site and the second layer is 0.015 to 0.55 µL per penetration pore.

9. A method for manufacturing the wound dressing according to claim 1, comprising the step of applying a hot-melt adhesive to the sheet material of the second layer, wherein the hot-melt adhesive covers a portion but not all of the water-repellent surface of the sheet material of the second layer, followed by stacking the first layer sheet material onto the water-repellent surface of the sheet material of the second layer to join both layers.

* * * * *